(12) United States Patent
Grande et al.

(10) Patent No.: US 8,501,442 B2
(45) Date of Patent: Aug. 6, 2013

(54) DETERMINATION OF 5-ASA EFFICACY IN CRC PREVENTION AND/OR TREATMENT BY GENE EXPRESSION ANALYSIS

(75) Inventors: Alexis Grande, Modena (IT); Sandra Parenti, Modena (IT); Fabrizio Ferrarini, Modena (IT)

(73) Assignee: Sofar SpA, Milan (IT)

( * ) Notice: Subject to any disclaimer, the term of this patent is extended or adjusted under 35 U.S.C. 154(b) by 283 days.

(21) Appl. No.: 12/662,275

(22) Filed: Apr. 8, 2010

(65) Prior Publication Data

US 2010/0261174 A1 Oct. 14, 2010

(30) Foreign Application Priority Data

Apr. 9, 2009 (EP) .................................. 09425136

(51) Int. Cl.
C12P 19/34 (2006.01)
(52) U.S. Cl.
USPC ........................................................ 435/91.2
(58) Field of Classification Search
None
See application file for complete search history.

(56) References Cited

PUBLICATIONS

Paterson et al. (2001) Q J Med vol. 94:445-448.*
Cell Signaling Technologies (created in Jan. 2003 and last revised in Nov. 2010).*
Bos et al. (2006) Oncogene 25:6447-6456.*
Bos et al. (2006) Carcinogenesis vol. 27 No. 12 pp. 2371-2382.*
Lassmann et al. (2002) J. Pathol 2002; 198:198-206.*
Parenti et al. (2010) Aliment Pharmacol Ther vol. 31: pp. 108-119.*
Allgayer, "Review article: mechanisms of action of mesalazine in preventing colorectal carcinoma in inflammatory bowel disease," Aliment Pharmacol Ther 18 (Supp 2):10-14, 2003.
Aoki et al., "Chromosomal instability by Beta-catenin/TCF transcription in APC or Beta-catenin mutant cells," Oncogene 26:3511-3520, 2007.
Bos et al., "Protein phophatase 2A is required for mesalazine-dependent inhibition of Wnt/beta-catenin pathway activity," Carcinogenesis 27(12):2371-2382, 2006.
Cheng and Desreumaux, "5-aminosalicylic acid is an attractive candidate agent for chemoprevention of colon cancer in patients with inflammatory bowel disease," World J Gastroenterol 11(3):309-314, 2005.
Chu et al., "Mesalazine downregulates c-Myc in human colon cancer cells. A key to its chemopreventive action?," Aliment Pharmacol Ther 25:1443-1449, 2007.
Evans and Liu, "Roles of Krueppel-like factor 4 in normal homeostasis, cancer and stem cells," Acta Biochim Biophys Sin 40(7):554-564, 2008.
Fevr et al., "Wnt/beta-catenin is essential for intestinal homeostasis and maintenance of intestinal stem cells," Molecular and Cellular Biology 27(21):7551-7559, 2007.

Gasche et al., "Mesalazine improves replication fidelity in cultured colorectal cells," Cancer Res 65(10):3993-3997, 2005.
Goldberg et al., "u-Protocadherin, a novel developmentally regulated protocadherin with mucin-like domains," J. of Biol Chem, 275(32):24622-24629, 2000.
Hou et al., "The fat1 cadherin integrates vascular smooth muscle cell growth and migration signals," J. Cell Biol, 173 (3):417-429, 2006.
Janne et al., "Chemoprevention of colorectal cancer," New England J. of Med 342(26):1960-1968, 2000.
Luciani et al., "5-ASA affects cell cycle progression in colorectal cells by reversibly activating a replication checkpoint," Gastroenterology 132:221-235, 2007.
Olmeda et al., "Beta-catenin regulation during the cell cycle: implications in G2/M and apoptosis," Molecular Biology of the Cell 14:2844-2860, 2003.
Palmer et al., "Vitamin D3 promotes the differentiation of colon carcinoma cells by the induction of E-cadherin and the inhibition of beta-catenin signaling," J. of Cell Bio 154(2):369-387, 2001.
Reinacher-Schick et al., "Mesalazine causes a mitotic arrest and induces caspase-dependent apoptosis in colon carcinoma cells," Carcinogenesis 24(3):443-451, 2003.
Rousseaux et al., "Intestinal antiinflammatory effect of 5-aminosalicyclic acid is dependent on peroxisome proliferator-activated receptor-gamma," J. of Experimental Medicine 201(8):1205-1215, 2005.
Rubin et al., "Colorectal cancer prevention in inflammatory bowel disease and the role of 5-aminosalicylci acid: a clinical review and update," Inflamm Bowel Dis 14(2):265-274, 2008.
Sandler et al., "A randomized trail of aspirin to prevent colorectal adenomas in patients with previous colorectal cancer," N Engl J Med 348(10):883-890 and a correction page, 2003.
Schuster and Porse, "C/EBPalpha: A tumour suppressor in multiple tissues?," Biochimica et Biophysica Acta 1766:88-103, 2006.
Stolfi et al., "Molecular basis of the potential of mesalazine to prevent colorectal cancer," World J Gastroenterol 14 (28):4434-4439, 2008.
Van De Wetering et al., "The beta-catenin/TCF-4 complex imposes a crypt progenitor phenotype on colorectal cancer cells," Cell 111:241-250, 2002.
Zhang et al., "Novel cross talk of krueppel-like factor 4 and beta-catenin regulates normal intestinal homeostasis and tumor repression," Molecular and Cellular Biology 26(6):2055-2064, 2006.
European Search Report in Serial No. EP 09 42 5136 dated Jul. 29, 2009, 8 pages.

* cited by examiner

*Primary Examiner* — Teresa E Strzelecka
*Assistant Examiner* — Suchira Pande
(74) *Attorney, Agent, or Firm* — Rothwell, Figg, Ernst & Manbeck P.C.

(57) ABSTRACT

A method is disclosed for the determination of 5-ASA efficacy in preventing and/or treating CRC in a mammalian, which comprises the analysis of the inhibition of the β-catenin pathway in presence of 5-ASA. More in details, the method comprises measuring the expression of at least one gene involved in the regulation of the β-catenin signalling pathway, such as μ-protocadherin, E-cadherin, β-catenin, Axin1, ICAT, $p21^{waf-1}$ and the expression of onco-suppressor genes, such as KLF4 and CEBPα. Gene expression can be measured in accordance to the methods commonly available in the art such as QRT-PCR and immunohistochemistry.

5 Claims, 5 Drawing Sheets

DETERMINATION OF 5-ASA EFFICACY IN CRC PREVENTION AND/OR TREATMENT BY GENE EXPRESSION ANALYSIS

The present invention is directed to a method for the determination of 5-ASA efficacy in preventing and/or treating CRC in a mammalian, which comprises the analysis of the inhibition of the β-catenin pathway and the activation of independent onco-suppressor genes in presence of 5-ASA. More in details, it is directed to a method for the determination of 5-ASA efficacy in preventing and/or treating CRC in a mammalian which comprises measuring the expression of at least one gene involved in the regulation of the β-catenin signalling pathway and of other onco-suppressor genes.

BACKGROUND ART

Non steroidal anti-inflammatory drugs (NSAIDs) are characterized by a well recognized chemopreventive activity against colorectal cancer (CRC)[1,2]. This activity has been observed in general population as well as in patients exhibiting an increased risk to develop the mentioned disease. Unfortunately the systemic and gastrointestinal toxicity of NSAIDs drastically limit their administration in the context of clinical protocols requiring a long term treatment of the involved patients. Both therapeutic and toxic effects elicited by these compounds are largely dependent on the inhibition of COX-1 and COX-2 enzymes that, in turn, is responsible for a reduced synthesis of prostaglandins (PG) normally mediating a number of biological functions. It is therefore possible to state that the pharmacological properties of NSAIDs substantially reside in their capacity to interfere with such functions. Several reports indicate that mesalazine (5 aminosalicylic acid or 5-ASA) can be a promising alternative to achieve a comparable anti-CRC chemopreventive activity, avoiding at the same time the side effects induced by NSAIDs[3-5]. In fact, in spite of the chemical similarity with aspirin, i.e a paradigmatic NSAID, 5-ASA is characterized by a weak COX inhibitory activity, a feature that clearly accounts for the clinical safeness of this therapeutic agent. Not surprisingly distinct mechanisms appear to mediate the anti-inflammatory effect of 5-ASA and, among them, an important role is probably played by the inhibition of transcription factors promoting the immune response such as NFkB and PPARs[6]. It has to be pointed out that the chemopreventive efficacy of 5-ASA has been, to date, exclusively demonstrated in patients affected by Inflammatory Bowel Diseases (IBD) (Crohn Disease and Ulcerative Colitis), characterized by an increased risk to develop CRC, and it remains to be confirmed in other individual categories such as healthy people or patients carrying genetic tumor syndromes. Although this issue can be univocally addressed through specifically designed clinical trials that could help to clarify the feasibility of anti-CRC chemoprevention with 5-ASA, an adequate characterization of the anti-tumor effects that this compound exerts at the cellular and molecular level could provide a fundamental contribute to such studies. The results of this investigation, in fact, could corroborate the biological rationale of clinical protocols analyzing the chemopreventive efficacy 5-ASA and allow the identification of biological markers able to monitor the pharmacological response to the considered treatment. In this regard, a growing body of evidence indicates that stimulation with 5-ASA determines a number of biological effects on colon cancer cells such as inhibition of proliferation, induction of apoptosis and enhancement of cell cycle checkpoints and DNA repair processes[7-10]. Interestingly 5-ASA has been recently demonstrated to interfere with the β-catenin signalling pathway by inhibiting the nuclear translocation of β-catenin, necessary to allow the transcription activity of this protein[11]. This observation could, in principle, explain virtually all the effects that 5-ASA induces on colon cancer cells since β-catenin has been implicated in the molecular control of G1/S[12,13] and G2/M[14,15] cell cycle transitions and indirectly also of apoptosis. In this patent we present the results of a set of experiments performed on the CaCo2 CRC cell line and aimed to better characterize the molecular mechanisms by which 5-ASA inhibits the β-catenin signalling pathway. The results obtained clearly demonstrated that this effect is at least in part mediated by the induction of a protein called µ-protocadherin that belongs to the cadherin superfamily and is able to sequester β-catenin on plasmatic membrane of 5-ASA treated CRC cells.

EFFECT OF THE INVENTION

The object of the present invention is therefore represented by an in vitro or ex vivo method for the determination of 5-ASA efficacy in preventing and/or treating CRC in a mammalian, preferably a human, possibly affected by CRC, which method comprises measuring the inhibition of the β-catenin pathway and the activation of independent onco-suppressor genes in presence of 5-ASA.

More in details, it is represented by a method for the determination of 5-ASA efficacy in preventing and/or treating CRC in a mammalian by measuring the expression of at least one gene involved in the regulation of the β-catenin signalling pathway and the expression of other onco-suppressor genes.

According to one embodiment, the method comprises isolating said at least one gene from said mammalian and measuring the expression thereof both in presence and in absence of 5-ASA: if the gene expression is higher in presence of 5-ASA than in absence thereof, 5-ASA will be thus effective in preventing and/or treating CRC in such a mammalian.

The preferred genes which are suitable for the method according to the present invention are preferably selected from µ-protocadherin, E-cadherin, β-catenin, Axin1, ICAT, p21$^{waf-1}$, KLF4 and CEBPα.

The gene expression can be measured in accordance to the methods commonly available in the art such as QRT-PCR and immunohistochemistry.

Results

Quantitative Real Time RT-PCR Analysis of Genes Regulating the β-catenin Signalling Pathway in CaCo2 Colon Adenocarcinoma Cells Exposed to 5-ASA Treatment.

Preliminary experiments performed in our laboratory confirmed that 5-ASA treatment inhibits the proliferation activity of CaCo2 cells. To investigate the molecular mechanisms underlying this effect we performed a microarray analysis, using the Affimetrix methodology, in order to assess the transcriptome changes determined on CaCo2 cells by treatment with 20 mM 5-ASA for 96 h. The results obtained revealed an up-regulated expression of a number of onco-suppressor genes, potentially explaining the anti-proliferative effect elicited by 5-ASA, among which the most important was represented by µ-protocadherin. This gene codes for a member of the cadherin superfamily and, based on previous reports by other authors, appeared as a putative inhibitor of the β-catenin signalling pathway, i.e. a cell proliferation pathway mediated by the activity of the β-catenin transcription factor[16,17]. The relevance of this finding resides in the observation that the β-catenin signalling pathway is constitutively activated in CRC. Other onco-suppressor genes up-regulated by 5-ASA treatment of the analyzed cells were represented by the KLF4 and CEBPα transcription factors, previously implicated in the proliferation inhibition of epithelial tumor cells in general and of CRC cells in particular[18-20]. To validate these data, the mRNA levels of the mentioned genes were analyzed by quantitative real time RT-PCR (QRT-PCR), in CaCo2 cells treated with 20 mM 5-ASA for 48 and 96 h. In addition, to better characterize the functional effect exerted by the investigated treatment on the β-catenin signalling pathway, we also included in this analysis other genes coding for the following proteins: β-catenin itself, i.e. the main component of the pathway; E-cadherin, for its ability to sequester β-catenin on the plasmatic membrane of cells; Axin1, due to its capacity to promote the activity of the β-catenin degradation complex; ICAT, responsible for the inhibition of β-catenin transcription in the nuclear compartment; $p21^{waf-1}$, previously implicated in growth arrest processes and also demonstrated to be a negative target of β-catenin. Up-regulation of mRNA expression resulted to be 12-fold for μ-protocadherin, 16-fold for $p21^{waf-1}$, 4 to 6-fold for KLF4 and CEBPα and 2 to 3-fold Axin 1 and ICAT. The most remarkable variations of expression were consequently observed for the μ-protocadherin and for the $p21^{waf-1}$ genes, suggesting that the β-catenin pathway was really inhibited under the adopted experimental conditions. The up-regulation of these genes appeared also more pronounced at the end of stimulation (96 h). mRNA expression of E-cadherin and β-catenin appeared, conversely, unaffected (FIG. 1).

Western Blot Analysis of μ-Protocadherin Protein Expression in CaCo2 Cells Treated with 5-ASA.

To confirm μ-protocadherin induction we performed a time course Western blot analysis on CaCo2 cells undergoing exposure to 20 mM 5-ASA for up to 96 h. The results of this set of experiments evidenced that μ-protocadherin protein was gradually but remarkably induced in the cytoplasmic extract of analyzed cells (FIG. 2).

Effect of 5-ASA Treatment on β-catenin Endocellular Levels in CaCo2 Cells.

Due to the particular regulation mechanisms controlling the β-catenin signalling pathway, levels of β-catenin protein observed in the different subcellular compartments represent reliable indicators of the extent of its activation. Based on this premise we performed an immunofluorescence assay to assess the sub-cellular distribution of β-catenin protein in CaCo2 cells undergoing treatment with 20 mM 5-ASA. The results obtained, presented in FIG. 3, provided a clear demonstration that, after 96 h of culture, β-catenin signal was localized in the nucleus and to a lesser extent in the cytoplasm of untreated cells whereas, in 5-ASA treated cells, it was almost exclusively localized in the plasmatic membrane. This set of experiments consequently suggested that 5-ASA treatment of CaCo2 cells interferes with nuclear translocation of β-catenin by sequestrating this protein on the plasmatic membrane of treated cells.

Coimmunoprecipitation Analysis of μ-protocadherin/β-catenin Protein Interaction.

The hypothesis arising from our data would directly imply that μ-protocadherin, as other proteins belonging to the cadherin superfamily, is able to bind β-catenin on the plasmatic membrane. To verify this interaction we performed co-immunoprecipitation experiments in which β-catenin was immunoprecipitated from lysates of CaCo2 cells treated with 20 mM 5-ASA for 96 h using a specific antibody and the immunoprecipitate was subsequently analyzed by Western blot carried out with a distinct antibody able to detect μ-protocadherin. By using this procedure we were able to demonstrate the presence of two immunoreactive μ-protocadherin bands, of 93 and 110 kDa respectively, interacting with β-catenin in 5-ASA treated CaCo2 cells (FIG. 4). Interestingly the 110 kDa form previously ascribed to a glycosilated version of the 93 kDa wild type protein by other authors, was exclusively observed in the β-catenin immunoprecipitate whereas it resulted undetectable in control samples (FIG. 4). This finding suggested that 110 kDa form of μ-protocadherin might be a post-translational modified version of the wild type protein characterized by a preferential binding activity to β-catenin.

Analysis of Biological Effects Promoted by 5-ASA Treatment of the HT29 Colon Adenocarcinoma Cell Line.

These findings were also confirmed in another colon adenocarcinoma cell line, named HT29, under the same experimental conditions. As shown in FIG. 5, a 96 h treatment of HT29 cells with 20 mM 5-ASA resulted in respectively a 3- and a 5-fold induction of μ-protocadherin and $p21^{waf-1}$ mRNA expression as assessed by QRT-PCR. These experiments consequently indicated that, although with less pronounced variations of the detected effects, HT29 cells exhibited a response to 5-ASA that was substantially comparable to that observed in CaCo2 cells.

EXAMPLE 1

Figure 1:
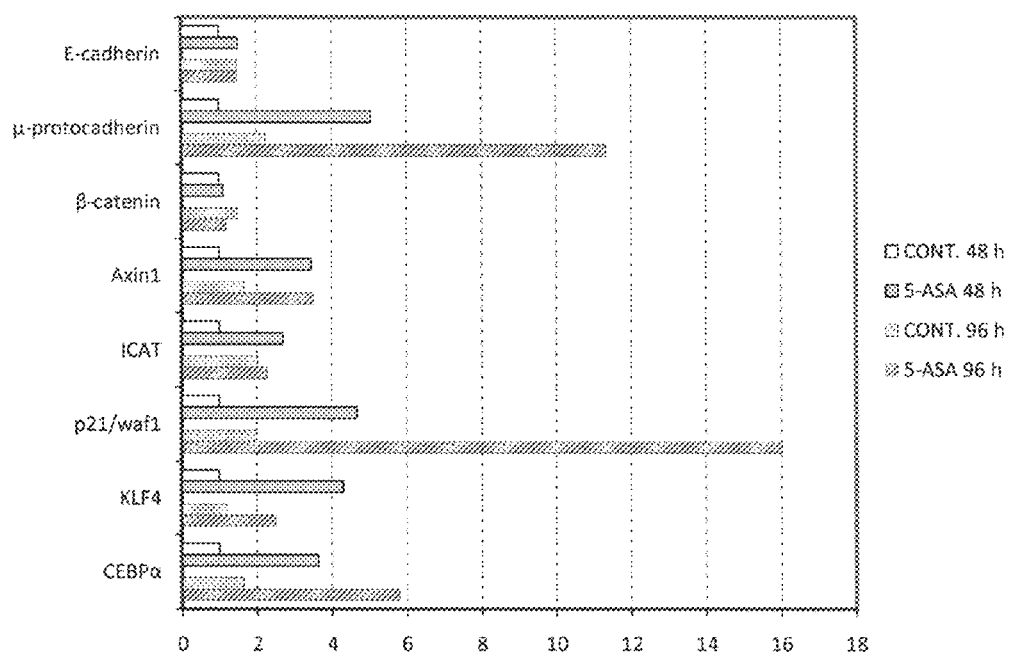
FIG. 1. QRT-PCR analysis of genes belonging to the β-catenin signalling pathway in CaCo2 cells treated with 5-ASA. Cells under the experimental conditions described in Results were analyzed by QRT-PCR to estimate the mRNA expression of genes belonging to the β-catenin signalling pathway, all indicated on y-axis. The effect determined by 5-ASA treatment on the mRNA expression of KLF4 and CEBPα onco-suppressor genes is also shown.
Figure 2:
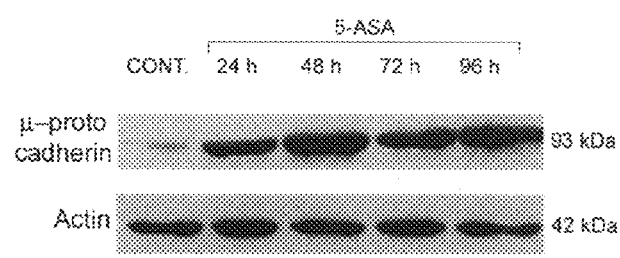
FIG. 2. Results of a time course Western blot analysis evaluating the expression of μ-protocadherin protein in CaCo2 cells treated with 5-ASA. This analysis was performed on cytoplasmic extracts of studied cells, at 24 h intervals following treatment with 5-ASA. Analyzed cell samples are indicated on the top. Normalization of the protein amount loaded in each lane was achieved using a pan-actin antibody able to detect either cytoplasmic or nuclear actin.
Figure 3:
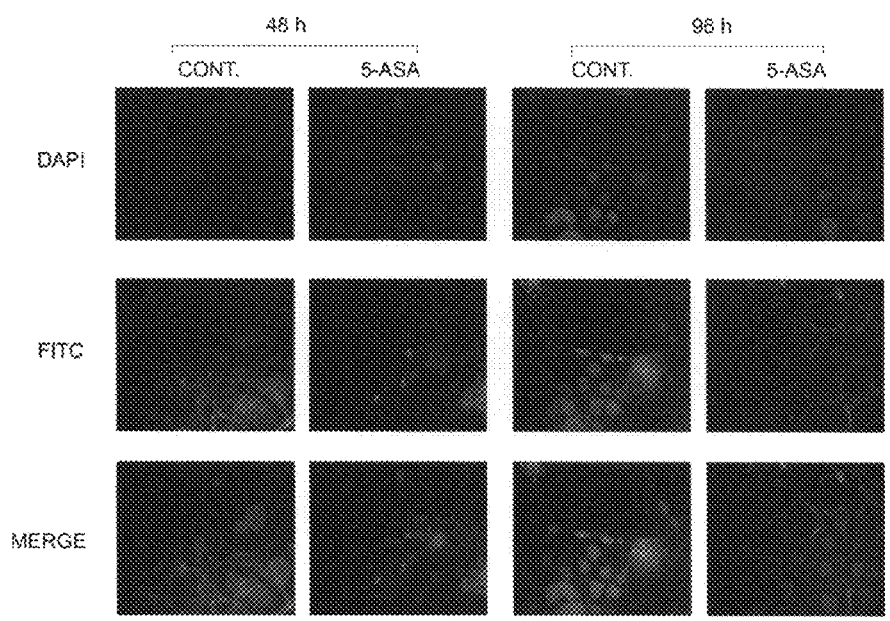
FIG. 3. Immunofluorescence analysis of β-catenin protein on CaCo2 cells exposed to 5-ASA treatment. Cells were stimulated with 5-ASA as explained in Results and subsequently stained with an anti-β-catenin primary antibody and a FITC conjugated secondary antibody (green fluorescence). Untreated control cells (CONT.) were also analyzed. Nuclei were counterstained with DAPI (blue fluorescence). Merge images, of the two analyzed fluorescence signals, are also shown.
Figure 4:
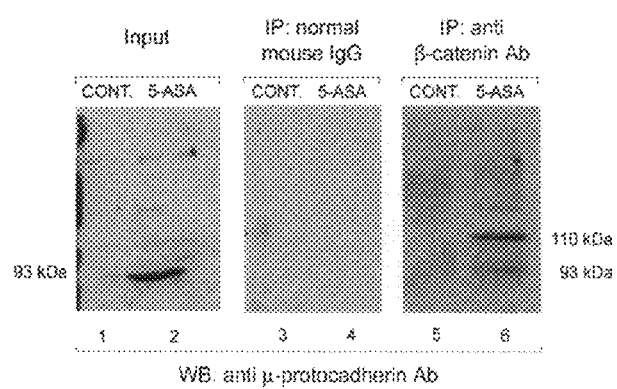
FIG. 4. Coimmunoprecipitation analysis of μ-protocadherin/β-catenin protein interaction. This figure shows the results on a coimmunoprecipitation analysis demonstrating the existence of a μ-protocadherin/β-catenin protein complex in 5-ASA treated CaCo2 cells. Western blot analysis of μ-protocadherin expression was performed in cell lysates of control untreated and 5-ASA treated CaCo2 cells (Input, left panel), immunoprecipitates obtained by the same cells using normal control IgG (middle panel) and immunoprecipitates obtained by the same cells using an anti-β-catenin antibody (right panel). IP, immunoprecipitation; WB, Western blot; Ab antibody.
Figure 5:
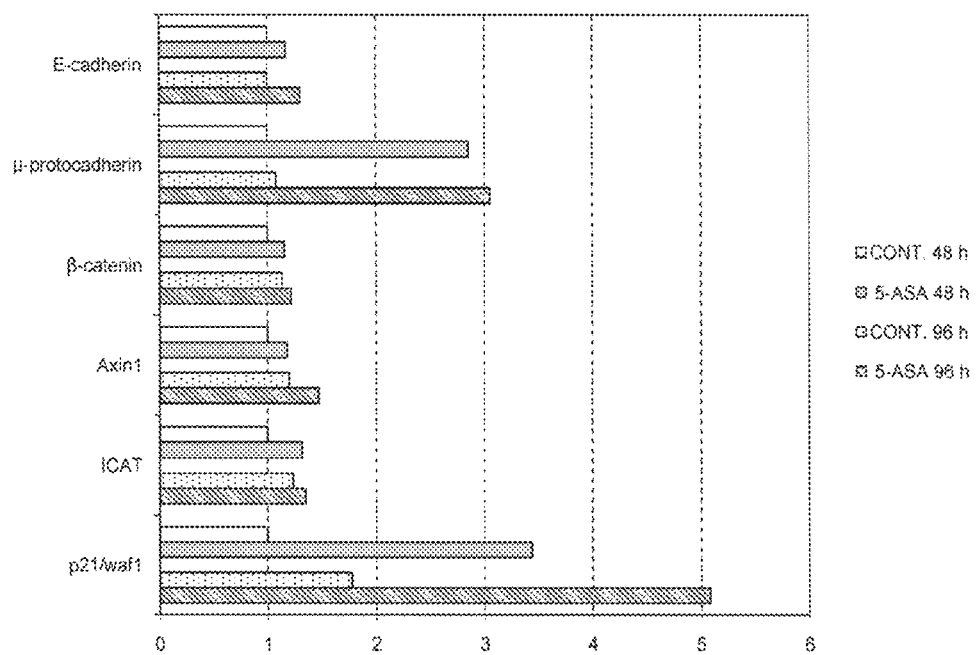
FIG. 5. Biological effects determined by treatment with 5-ASA on the HT29 colon adenocarcinoma cell line. The mRNA expression variations of gene belonging to the β-catenin signalling pathway were analyzed in HT29 cells using the QRT-PCR reaction under the experimental conditions described in Results and in FIG. 1.

Analysis of Gene Expression by Quantitative Real Time PCR (QRT-PCR)

Total RNA was extracted from cell suspensions and frozen tissues by means of the Qiagen total RNA purification kit as recommended by the manufacturer (Qiagen, Valencia, Calif.). RNA integrity and concentration were verified using the Bio-Analyzer technique (Applied Biosystem, Foster City, Calif.). 100 ng of total RNA were reverse transcribed using the High Capacity cDNA Archive Kit (Applied Biosystems) according to the manufacturer's instructions. QRT-PCR was performed with an ABI PRISM 7900 sequence detection system (Applied Biosystems) to quantify the relative levels of mRNA in the samples. Primers and probes for mRNA amplification of μ-protocadherin, E-cadherin, β-catenin, Axin-1, Inhibitor of β-Catenin and TCF-4 (ICAT), $p21^{waf-1}$, KLF4, CEBPα, and glyceraldehyde-3-phosphate dehydrogenase (GAPDH) were designed by Applied Biosystems. Each cDNA sample was run in triplicate in 50 μl reaction volume using Taqman Universal PCR Master Mix (Applied Biosystems). Thermal cycling was started with an initial denaturation at 50° C. for 2 min and 95° C. for 10 min, followed by 40 thermal cycles of 15 sec at 95° C. and 1 min at 60° C. Evaluation of QRT-PCR signals was performed using the ΔΔCt relative quantitation method. This procedure calculates the relative changes in gene expression of the target gene normalized to the endogenous control (GAPDH) and compared to a calibrator sample. The values obtained were expressed in terms of relative quantity (RQ) of mRNA level variation.

EXAMPLE 2

Analysis of μ-Protocadherin Expression by Immunohistochemical Assay

Sample sections (4 μm) were cut from paraffin blocks and deparaffinized using standard methods. Briefly, deparaffinization was carried out with xylol; sections were then rehydrated using graded ethanol till water and treated with a methanol-hydrogen peroxide (6%) solution for 15 minutes. Sections were then washed three times with PBS (phosphate buffer) and incubated with a primary anti-μ-protocadherin antibody (rabbit anti-mucdh1, Sigma Prestige HPA009173) at room temperature. The antibody was detected adding a biotinylated anti-rabbit secondary antibody, a streptavidin—peroxidase complex and 3,3'-diaminobenzidine used as chromogen. The slides were then hematoxylin counterstained.

References
1. Janne P A, Mayer R J. Chemoprevention of colorectal cancer. N Engl J Med 2000;342:1960-8.
2. Sandler R S, Halabi S, Baron J A, Budinger S, Paskett E, Keresztes R, Petrelli N, Pipas J M, Karp D D, Loprinzi C L, Steinbach G, Schilsky R. A randomized trial of aspirin to prevent colorectal adenomas in patients with previous colorectal cancer. N Engl J Med 2003;348:883-90.
3. Stolfi C, Pellegrini R, Franze E, Pallone F, Monteleone G. Molecular basis of the potential of mesalazine to prevent colorectal cancer. World J Gastroenterol, 2008;14:4434-9.
4. Cheng Y, Desreumaux P. 5-aminosalicylic acid is an attractive candidate agent for chemoprevention of colon cancer in patients with inflammatory bowel disease. World J Gastroenterol 2005;11:309-14.
5. Allgayer H. Review article: mechanisms of action of mesalazine in preventing colorectal carcinoma in inflammatory bowel disease. Aliment Pharmacol Ther 2003;18 Suppl 2:10-4.
6. Rousseaux C, Lefebvre B, Dubuquoy L, Lefebvre P, Romano O, Auwerx J, Metzger D, Wahli W, Desvergne B, Naccari G C, Chavatte P, Farce A, Bulois P, Cortot A, Colombel J F, Desreumaux P. Intestinal antiinflammatory effect of 5-aminosalicylic acid is dependent on peroxisome proliferator-activated receptor-gamma. J Exp Med 2005; 201:1205-15.
7. Reinacher-Schick A, Schoeneck A, Graeven U, Schwarte-Waldhoff I, Schmiegel W. Mesalazine causes a mitotic arrest and induces caspase-dependent apoptosis in colon carcinoma cells. Carcinogenesis 2003;24:443-51.
8. Gasche C, Goel A, Natarajan L, Boland C R. Mesalazine improves replication fidelity in cultured colorectal cells. Cancer Res 2005;65:3993-7.
9. Chu E C, Chai J, Ahluwalia A, Tarnawski A S. Mesalazine downregulates c-Myc in human colon cancer cells. A key to its chemopreventive action? Aliment Pharmacol Ther 2007;25:1443-9.
10. Luciani M G, Campregher C, Fortune J M, Kunkel T A, Gasche C. 5-ASA affects cell cycle progression in colorectal cells by reversibly activating a replication checkpoint. Gastroenterology 2007;132:221-35.
11. Bos C L, Diks S H, Hardwick J C, Walburg K V, Peppelenbosch M P, Richel D J. Protein phosphatase 2A is required for mesalazine-dependent inhibition of Wnt/beta-catenin pathway activity. Carcinogenesis 2006;27:2371-82.
12. Van de Wetering M, Sancho E, Verweij C, de Lau W, Oving I, Hurlstone A, van der Horn K, Bathe E, Coudreuse D, Haramis A P, Tjon-Pon-Fong M, Moerer P, van den Born M, Soete G, Pals S, Eilers M, Medema R, Clevers H. The beta-catenin/TCF-4 complex imposes a crypt progenitor phenotype on colorectal cancer cells. Cell 2002;111:241-50.
13. Fevr T, Robine S, Louvard D, Huelsken J. Wnt/beta-catenin is essential for intestinal homeostasis and maintenance of intestinal stem cells. Mol Cell Biol 2007;27:7551-9.
14. Olmeda D, Castel S, Vilaro S, Cano A. Beta-catenin regulation during the cell cycle: implications in G2/M and apoptosis. Mol Biol Cell 2003;14:2844-60.
15. Aoki K, Aoki M, Sugai M, Harada N, Miyoshi H, Tsukamoto T, Mizoshita T, Tatematsu M, Seno H, Chiba T, Oshima M, Hsieh C L, Taketo M M. Chromosomal instability by beta-cateninlTCF transcription in APC or beta-catenin mutant cells. Oncogene 2007;26:3511-20.
16. Palmer H G, Gonzalez-Sancho J M, Espada J, Berciano M T, Puig I, Baulida J, Quintanilla M, Cano A, de Herreros A G, Lafarga M, Munoz A. Vitamin D(3) promotes the differentiation of colon carcinoma cells by the induction of E-cadherin and the inhibition of beta-catenin signaling. J Cell Biol 2001;154:369-87.
17. Hou R, Liu L, Anees S, Hiroyasu S, Sibinga N E. The Fat1 cadherin integrates vascular smooth muscle cell growth and migration signals. J Cell Biol 2006;173:417-29.
18. Evans P M, Liu C. Roles of Krüpel-like factor 4 in normal homeostasis, cancer and stem cells. Acta Biochim Biophys Sin (Shanghai). 2008 July;40(7):554-64. Review.
19. Zhang W, Chen X, Kato Y, Evans P M, Yuan S, Yang J, Rychahou P G, Yang V W, He X, Evers B M, Liu C. Novel cross talk of Kruppel-like factor 4 and beta-catenin regulates normal intestinal homeostasis and tumor repression. Mol Cell Biol. 2006 March;26(6):2055-64.

20. Schuster M B, Porse B T. C/EBPalpha: a tumour suppressor in multiple tissues? Biochim Biophys Acta. 2006 August;1766(1):88-103. Epub 2006 Mar. 24. Review. PMID: 16616425 [PubMed-indexed for MEDLINE].

The invention claimed is:

1. A method for determination of the effect of 5-aminosalicylic acid (5-ASA) on mammalian colorectal cancer cells in vitro or ex vivo, which method comprises measuring the inhibition of the β-catenin pathway in the presence of 5-ASA by measuring the expression of a μ-protocadherin gene.

2. The method according to claim 1, which comprises isolating the μ-protocadherin gene from said mammal and measuring the expression thereof both in presence and in absence of 5-ASA.

3. The method according to claim 1, wherein the expression of the μ-protocadherin gene is measured by QRT-PCR and immunohistochemistry.

4. The method according to claim 1, wherein said mammal is a human.

5. The method of claim 1, which further comprises measuring the expression of Krüppel-like factor 4 (KLF4) gene and the CCAAT-enhancer binding protein α (CEBPα) gene.

* * * * *